United States Patent
Aubert et al.

(10) Patent No.: US 11,464,670 B2
(45) Date of Patent: Oct. 11, 2022

(54) DEVICE FOR LOCALIZED COOLING OF AN ORGAN

(71) Applicants: COMMISSARIAT A L'ENERGIE ATOMIQUE ET AUX ENERGIES ALTERNATIVES, Paris (FR); UNIVERSITE GRENOBLE ALPES, Saint Martin d'heres (FR); CENTRE HOSPITALIER UNIVERSITAIRE GRENOBLE ALPES, La Tronche (FR)

(72) Inventors: Nicolas Aubert, Grenoble (FR); Claude Chabrol, Poisat (FR); Stephan Chabardes, Venon (FR); Laurent Duraffourg, Voiron (FR)

(73) Assignees: COMMISSARIAT A L'ENERGIE ATOMIQUE ET AUX ENERGIES ALTERNATIVES, Paris (FR); UNIVERSITE GRENOBLE ALPES, Saint Martin d'heres (FR); CENTRE HOSPITALIER UNIVERSITAIRE GRENOBLE ALPES, La Tronche (FR)

( * ) Notice: Subject to any disclaimer, the term of this patent is extended or adjusted under 35 U.S.C. 154(b) by 854 days.

(21) Appl. No.: 16/332,630

(22) PCT Filed: Sep. 12, 2017

(86) PCT No.: PCT/FR2017/052423
§ 371 (c)(1),
(2) Date: Mar. 12, 2019

(87) PCT Pub. No.: WO2018/051005
PCT Pub. Date: Mar. 22, 2018

(65) Prior Publication Data
US 2021/0282963 A1   Sep. 16, 2021

(30) Foreign Application Priority Data
Sep. 15, 2016   (FR) ...................... 1658654

(51) Int. Cl.
*A61F 7/12*   (2006.01)
*H01S 3/00*   (2006.01)
(Continued)

(52) U.S. Cl.
CPC ............... *A61F 7/12* (2013.01); *H01S 3/005* (2013.01); *A61F 2007/0002* (2013.01);
(Continued)

(58) Field of Classification Search
CPC combination set(s) only.
See application file for complete search history.

(56) References Cited

U.S. PATENT DOCUMENTS 5,447,032 A   9/1995  Epstein et al.
5,620,571 A   4/1997  Bahns et al.
(Continued)

FOREIGN PATENT DOCUMENTS

JP   2006-15064 A   1/2006
WO   WO 2016/102351 A1   6/2016

OTHER PUBLICATIONS

International Search Report dated Jan. 16, 2018 in PCT/FR2017/052423 filed on Sep. 12, 2017.
(Continued)

*Primary Examiner* — Joseph A Stoklosa
*Assistant Examiner* — Adam J Avigan
(74) *Attorney, Agent, or Firm* — Oblon, McClelland, Maier & Neustadt, L.L.P.

(57) ABSTRACT

The invention relates to a device for cooling an organ locally, that includes an elongate stem including a far end intended to make contact with an organ to be cooled and comprising including a cooling element having a cold finger, a crystal that has a capacity to cool via excitation at a set excitation wavelength, said crystal being positioned adjacent to said cooling element, an optical guide that is able to
(Continued)

convey a light signal at said excitation wavelength and that opens onto said crystal, and an illuminating system including at least one light source, which light source is arranged to emit said light signal.

10 Claims, 2 Drawing Sheets

(51) Int. Cl.
   *A61F 7/00*     (2006.01)
   *F28D 21/00*    (2006.01)
(52) U.S. Cl.
   CPC .............. *A61F 2007/0088* (2013.01); *A61F 2007/0096* (2013.01); *A61F 2007/126* (2013.01); *F28D 21/0001* (2013.01); *F28D 2021/005* (2013.01)

(56) References Cited

U.S. PATENT DOCUMENTS

| | | | |
|---|---|---|---|
| 5,928,222 A * | 7/1999 | Kleinerman | G01K 11/3213 606/15 |
| 6,041,610 A * | 3/2000 | Edwards | F25B 23/003 62/3.1 |
| 7,204,833 B1 * | 4/2007 | Osorio | A61B 5/4094 607/105 |
| 8,720,219 B1 | 5/2014 | Sheik-Bahae | |
| 9,362,712 B1 | 6/2016 | Sheik-Bahae et al. | |
| 2007/0005121 A1 | 1/2007 | Khanna | |
| 2009/0005843 A1 * | 1/2009 | Smyth | A61F 7/12 607/113 |
| 2009/0137997 A1 * | 5/2009 | Zhang | A61B 18/24 606/11 |
| 2012/0221082 A1 | 8/2012 | Khanna | |
| 2017/0325994 A1 | 11/2017 | Khanna | |
| 2017/0361122 A1 | 12/2017 | Chabrol et al. | |
| 2018/0329240 A1 * | 11/2018 | Raghu | H05K 1/181 |

OTHER PUBLICATIONS

Seletskiy, D. V. et al., "Laser cooling of a semiconductor load to 165 K", Optics Express, vol. 18, No. 17, Aug. 16, 2010, pp. 18061-18066.

Melgaard, S. D. et al., "Solid-state optical refrigeration to sub-100 Kelvin regime", Scientific Reports, vol. 6, No. 20380, Feb. 5, 2016, total 6 pages.

Epstein, R. I. et al., "Observation of laser-induced fluorescent cooling of a solid", Nature, vol. 377, Oct. 12, 1995, pp. 500-503.

* cited by examiner

DEVICE FOR LOCALIZED COOLING OF AN ORGAN

TECHNICAL FIELD OF THE INVENTION

The present invention relates to a device for cooling an organ, such as for example the human brain, locally.

PRIOR ART

It is known to treat certain diseases by carrying out localized cooling of tissues. This is for example the case of diseases, such as epilepsy, in which localized cooling of the epileptogenic zone allows the onset of seizures to be blocked or their propagation to be limited. This is of interest to patients afflicted with this pathology and who cannot be treated, because of a pharmacoresistant character, with conventional drugs. However, cooling devices are often not very suitable for chronic intra-cerebral implantation. Certain known solutions, which are not suitable for implantation, are for example based on microfluidic principles and use thermoelectric modules.

Various solutions are described in the documents referenced US2007/005121A1, JP2006/015064A, U.S. Pat. Nos. 5,620,571A, 9,362,712B1 and WO2016/102351A1.

The aim of the invention is thus to propose a cooling device that has a configuration suitable for long-term implantation, that minimizes medical risks both during its implantation and during its operation, and that is able to turn on on command at any time in a closed-loop mode—for example during the onset of an epileptic seizure.

SUMMARY OF THE INVENTION

This aim is achieved via a device for cooling an organ locally comprising:
  An elongate stem comprising a far end intended to make contact with an organ to be cooled and comprising:
    A cooling element comprising a cold finger,
    A crystal that has a capacity to cool via excitation at a set excitation wavelength, said crystal being positioned adjacent to said cooling element,
    An optical guide that is able to convey a light signal at said excitation wavelength and that opens onto said crystal,
    An illuminating system comprising at least one light source, which light source is arranged to emit said light signal.

According to one particularity, the device comprises a cavity in which said crystal is housed. The cooling element is preferably positioned in proximity to said cavity so as to ensure the transfer of heat between the cooling crystal and its cold finger.

According to another particularity, the cooling element comprises a heat exchanger that is placed between the cold finger and the cavity enclosing the crystal.

According to another particularity, the device comprises at least one second optical guide that is arranged along the stem and that opens onto said crystal so as to remove or monitor the fluorescence level emitted by the excitation of the crystal.

Advantageously, the device comprises a processing and control unit arranged to control said illuminating system.

Advantageously, it comprises a temperature sensor arranged to determine the temperature of the crystal.

According to one particularity, said temperature sensor comprises means for determining the temperature of the crystal from the wavelength of the light signal emitted by the light source.

Advantageously, the stem is formed by an overmolding made of silicone or polyurethane.

Preferably, the crystal is of Yb:YLF, Zb:LANP or Tm:Yb:YLF type.

Advantageously, the light source of the device is chosen among:
  a laser diode,
  a fiber laser,
  a DPSS (diode-pumped solid-state) laser, or
  an OPS (optically-pumped semiconductor) laser.

The device of the invention will notably be incorporated into a system that operates in a closed-loop mode and that employs suitable detecting means. The detecting means are for example arranged to detect an epileptogenic focus and the device of the invention is then suitable for generating cooling of suitable intensity in order to then contribute to the stoppage of the seizure or to block its onset.

BRIEF DESCRIPTION OF THE FIGURES

Other features and advantages will become apparent from the following detailed description given with reference to the appended drawings, in which.

DETAILED DESCRIPTION OF AT LEAST ONE EMBODIMENT

The invention relates to a device for cooling an organ locally with a view to cooling the tissues thereof. Said organ will for example be the human brain.

Nonlimitingly, the device of the invention will for example be suitable for treating various pathologies, for example:
  Epileptic seizures,
  Cranioencephalic trauma,
  Neuro-Cancer,
  Parkinson's disease or other movement disorders such as dystonia, essential tremors, Huntington's disease.

Of course, given certain adaptations, it will be understood that the device will possibly be employed to treat other pathologies.

In the case of treatment of an epileptic seizure, the source of generated cold is intended to be placed in contact with epileptogenic foci or with any other zone of the brain 30 that is surgically accessible using stereotactic mini-invasive methods via a cranial drill hole of a few millimeters. The cooling generated then contributes to stoppage of the seizure or to blockage of the onset thereof.

The invention takes the form of a device 1 for cooling locally, which is biocompatible and implantable so as to be able to act on command at any time, for example when the onset of an epileptic seizure is detected, using algorithms for detecting seizures in a closed-loop mode.

Figure 1:
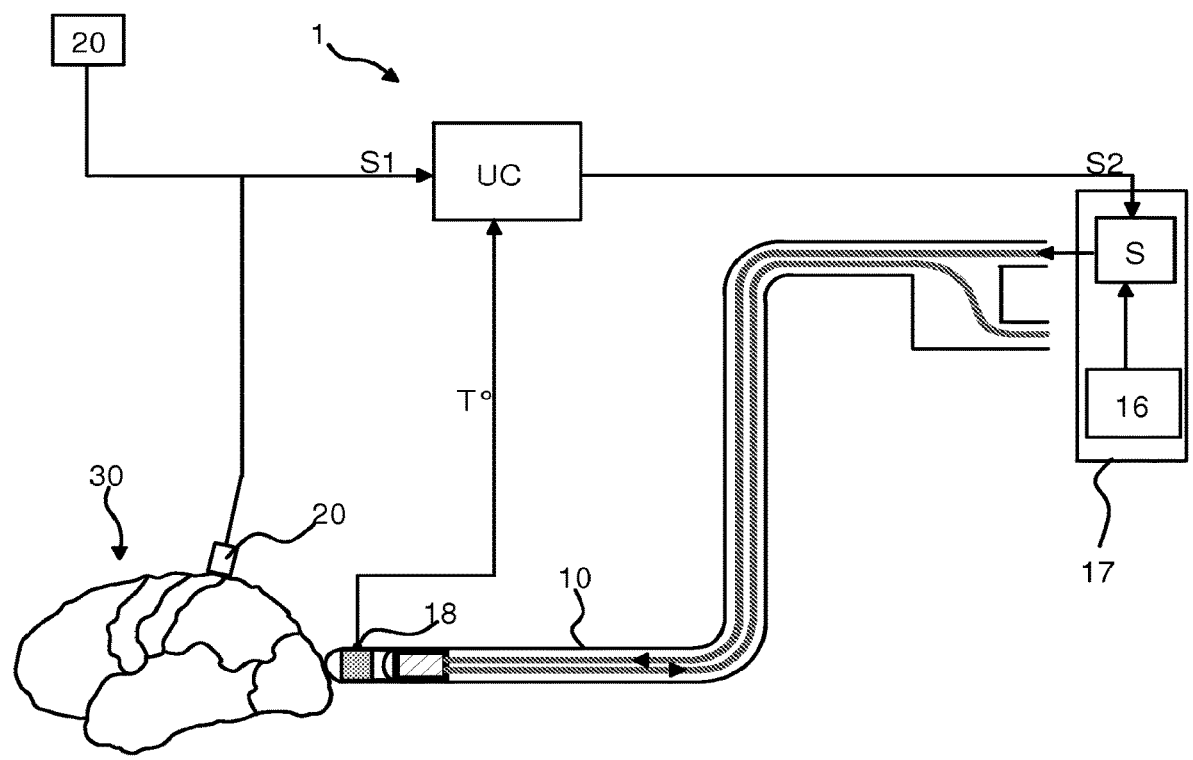
FIG. 1 schematically shows the architecture of the cooling device of the invention.

In the targeted application, detecting means 20, which are not the subject of the present patent application, are for example employed to detect the onset of the pathology to be treated. In the case of an epileptic seizure, these detecting means 20 are implanted in the skull in order to monitor an epileptogenic zone (FIG. 1). When the onset of a seizure is detected, the detecting means 20 send a signal S1 to a processing and control unit UC. The processing and control unit UC then transmits a command (S2) to the cooling device of the invention. The cooling device of the invention is controlled to generate cooling that is suitable for the treated pathology. If it is a question of an epileptic seizure, the intensity of the cooling and its duration of application will preferably be related to the intensity level of the seizure, which will have been measured by the detecting means 20. To generate a command that is suitable for the cooling device, the processing and control unit UC preferably comprises an analyzing module that is intended to analyze the signal S1 received from the detecting means and to determine a suitable treatment.

The processing and control unit UC advantageously forms part of the cooling device 1 of the invention. It comprises at least one microprocessor and a memory. It is intended to execute software instructions that are representative of a sequence of treatment of the pathology by the device. It notably comprises means for controlling an illuminating system that will be detailed below. It also comprises one or more communication interfaces that are intended to communicate with various entities, notably the detecting means described above. The communication links will possibly be wired or wireless.

The cooling device 1 of the invention takes the form of at least one elongate stem 10 made of supple material comprising a far end intended to make contact with the organ to be cooled. The cross section of this supple stem 10 is preferably circular. The area of the cross section of the stem is sufficiently small for it to be easily implantable during a conventional surgical operation. In the case of a stem of circular cross section, its diameter is comprised between 0.5 and 3 mm, and advantageously between 1 and 2.5 mm. At its near end, the stem 10 advantageously comprises connectors of optical nature for connection to a light source and of electrical nature for connection to the processing and control unit.

Of course, the device of the invention is produced from biocompatible materials in order to be able to be implanted in a living being.

The stem 10 is formed by an overmolding made of supple material that incorporates the various elements that are described below. These elements are therefore advantageously covered by this overmolding, which is for example made of silicone or of polyurethane. This overmolding notably allows any leakage of physiological liquids to be avoided.

The device 1 thus comprises a cooling element 11 that comprises a cold finger 110 that is located at the far end of the stem 10 and that is intended to make contact with the organ to be cooled (brain 30 in FIG. 1).

The device 1 comprises a cavity 12 that is incorporated into the stem and a cooling crystal 13 that is housed in said cavity 12. The crystal 13 is placed in the cavity and fastened to the latter by materials that do not absorb the light produced and that conduct heat poorly. The cooling element 11 is intended to sense the negative temperature variation generated by the cooling crystal when the latter is suitably excited. The cooling element is preferably positioned as close as possible to said cavity 12 for a better transfer of heat between the walls of said cavity and said cooling element.

The cooling crystal 13 is preferably formed from a material suitable for operating according to what is called an "anti-Stokes fluorescence" principle. This principle consists of inelastic scattering of light, implying an exchange of energy between an incident photon of a light signal having struck the crystal at a set wavelength and the crystal. The light scattered by the crystal thus does not have the same wavelength as the incident light. In the case of an anti-Stokes shift, the scattered light has a shorter wavelength than the incident light but a higher energy, this leading to cooling of the crystal.

Nonlimitingly, the crystal employed will preferably be formed from any low-phonon-energy ytterbium-doped host matrix. It will for example be a crystal of Yb:YLF type. The excitation wavelength thereof is comprised between about 1010 nm and 1040 nm.

Of course, any other crystal composition will possibly be envisioned, such as for example that of a crystal of YLF co-doped with 5% Yb and 0.0016% Tm. Particular attention will be given to the purity of the crystals used. For example, components of 5N purity will be used in the manufacture of the host matrix.

Figure 3:
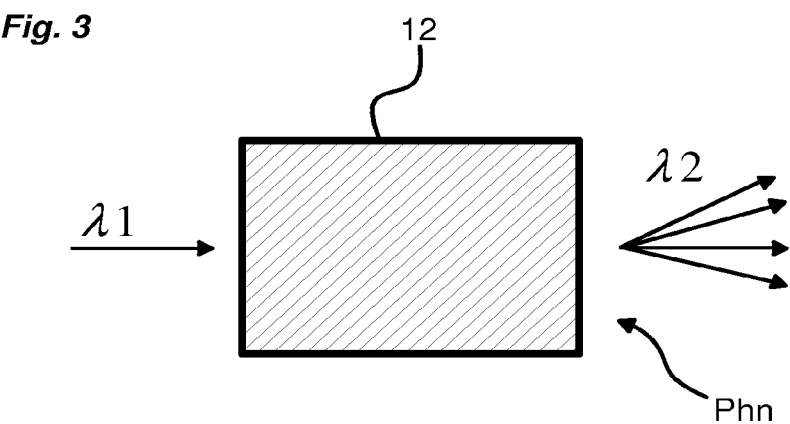
FIG. 3 illustrates the operating principle of the cooling crystal.

In the case of a crystal doped with ytterbium, the cooling scheme is as follows: an electron initially occupying level E4 will be raised to an excited state E5 by absorption of an incident photon of 1020 nm wavelength (illustrated by the excitation wavelength $\lambda 1$ in FIG. 3). It is then raised to state E6 by absorption of a phonon (Phn in FIG. 3). This electron decays radiatively to the level E2 by emitting a photon of 1000 nm wavelength (reemission wavelength $\lambda 2$ in FIG. 3). Another phonon is absorbed before the electron returns to its original state. FIG. 3 illustrates the operating principle of such a crystal.

As a variant embodiment, the employed crystal will possibly make use of Brillouin scattering. Just like the aforementioned anti-Stokes fluorescence, this scattering is also inelastic scattering in a crystal illuminated by laser. The only difference resides in the fact that the wavelength shift is smaller and dependent on the wavelength of the excitation laser.

Figure 2A:
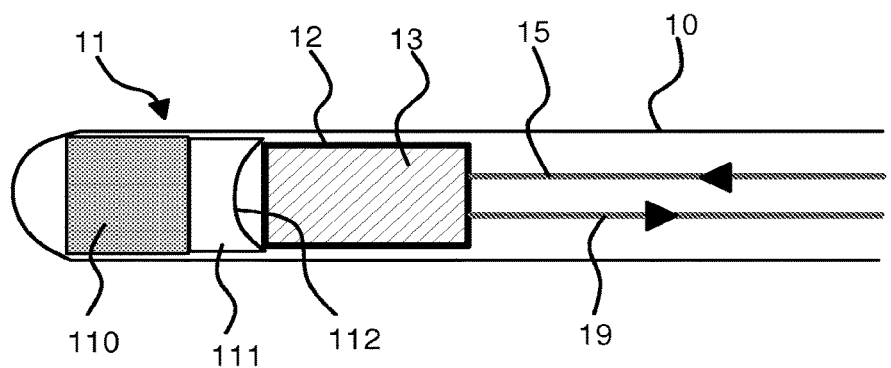
FIG. 2A shows in detail and schematically the architecture of the far end of the cooling device of the invention, according to a first embodiment.

In a first embodiment shown in FIG. 2A, the cooling element 11 comprises a heat exchanger 111 connecting its cold finger 110 to the assembly made up of the crystal and of the cavity and allowing the temperature variation undergone by the crystal to be transmitted to the cold finger.

The heat exchanger is chosen so as to minimize the temperature gradient produced between the crystal and the cold finger. By way of example, the heat exchanger 111 is made of sapphire. Advantageously, a dielectric treatment is produced at the junction between the crystal 13 and the heat exchanger 111 made of sapphire.

Advantageously, the cooling element 11 comprises a plano-concave mirror 112 that is arranged between the heat exchanger and the crystal and that is intended to reflect the radiation incident on the crystal. This mirror is HR (highly reflective) in the visible wavelength range [400-700] and in the IR wavelength range [900-1100].

In the arrangement described above, the elements consisting of the cold finger 110, of the heat exchanger 111 and of the cavity 12 enclosing the crystal 13 are positioned adjacently and so as to make contact with one another. The material of the stem forming the overmolding therefore does not get between these elements, in order not to disrupt operation of the device.

Figure 2B:
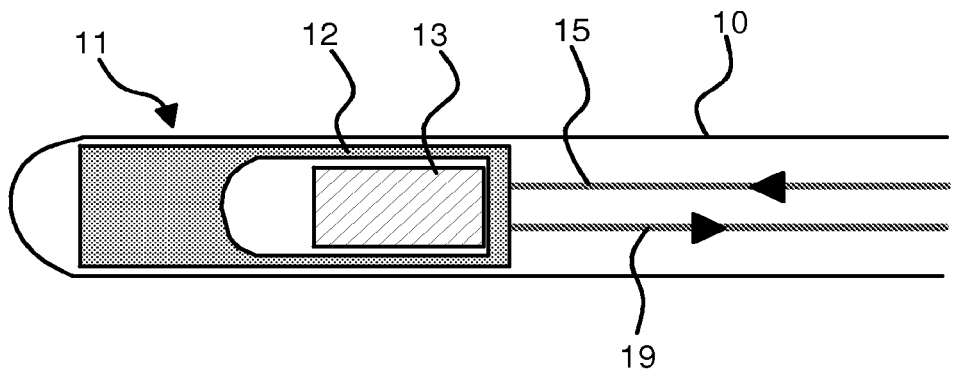
FIG. 2B shows, in detail and schematically, the architecture of the far end of the cooling device of the invention, according to a second embodiment.

According to one variant embodiment shown in FIG. 2B, the cooling element 11 takes the form of an element of integral construction, in which element said cavity that hermetically encloses the crystal is produced. The cooling element 11 therefore plays both the role of heat exchanger and the role of cold finger. The cooling element 11 is then preferably manufactured from sapphire or titanium. As described above, it is covered with an overmolding made of silicone. It also incorporates the plano-concave mirror defined above, this mirror then forming an internal wall of the cavity 12 that houses the crystal 13.

As described above, the crystal 13 generates cold when it is illuminated by an incident light signal. To this end, the device comprises at least one first optical guide 15 that extends along the stem from its near end to the crystal located at its far end. The optical guide 15 is arranged to open onto the cavity 12 in which the crystal 13 is housed with a view to being able to convey light to said cavity 12. The light signal is generated at a set wavelength in order to excite the crystal.

According to the invention, to remove the light produced by the crystal 13 by fluorescence, a plurality of options are envisionable:
Let the light produced diffuse into the biological tissue (said light is located in the 700 nm to 1000 nm minimum absorption window). It will thus end up being absorbed (absorption of 0.1 to 0.5 $cm^{-1}$) far from the crystal without creating harmful heating.
Trap the light produced in the cavity in which the crystal is located then remove it via associated fiber-optic channels. In this configuration, the device advantageously comprises, in parallel to the first optical guide, one or more other optical guides 19 that are intended to remove or monitor the level of light generated by the crystal by fluorescence during the excitation. In FIGS. 1 and 2, a single "return" optical guide is shown but it will be understood that a plurality of additional guides may be employed.

Depending on the employed configuration the internal and external walls of the cavity will be treated in different ways:
Treatment that is HR in the visible, and
Treatment that is HT in the infrared, if return optical guide absent, or
Treatment that is HR in the infrared if return optical guide present.

To generate the excitation light signal sent through the first optical guide, the device advantageously incorporates an illuminating system 17. The illuminating system 17 comprises a light source S that is employed to emit the excitation light signal that is intended for the crystal 13 through the optical guide 15. The source S will possibly be of various types, and for example formed by:
a laser diode,
a fiber laser,
a DPSS (diode-pumped solid-state) a laser, or
an OPS (optically-pumped semiconductor) laser.

Advantageously, the exit of the source S will be connected directly to the optical guide 15 of the device 1.

The illuminating system 17 of course comprises an electrical power supply 16 that is preferably housed in a hermetic casing. According to two distinct variant embodiments, the light source S of the illuminating system is either incorporated into said casing or located remotely from this casing. In the first case, the source S is coupled to the optical guide 15 by way of a demountable connector.

As described above, the illuminating system 17 is controlled by means for controlling the processing and control unit UC. These control means are intended to transmit a control signal S2 to the illuminating system when a seizure is detected. The processing and control unit UC is advantageously housed in said hermetic casing and supplied with power by said electrical power supply 16.

Nonlimitingly, the electrical power supply 16 of the device 1 will possibly comprise a rechargeable battery, a nonrechargeable battery or employ a power-generating solution, for example one using an electromagnetic generator that comprises an antenna intended to generate an induced electric current. Any other solution could of course be envisioned, such as a generator of power from mechanical vibrations or a thermoelectric generator.

The cooling device 1 preferably incorporates a temperature sensor 18 for determining the temperature of the crystal 13. The temperature data measured by the sensor are advantageously sent to the processing and control unit UC with a view to controlling in real-time the cooling level applied by the device of the invention and to adjusting it if necessary by executing a temperature adjustment loop.

Figure 4:
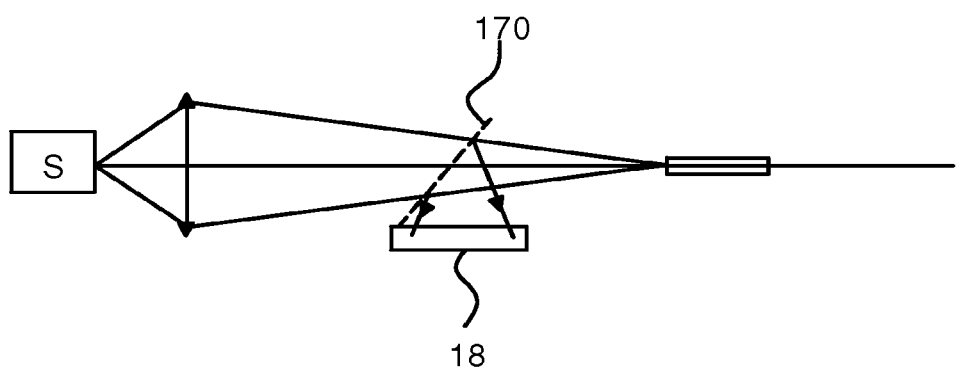
FIG. 4 illustrates the operating principle of a sensor for determining the temperature of the crystal from the wavelength of the emitted light.

The employed temperature sensor for example uses an optical measuring technology. FIG. 4 illustrates the operating principle of such a sensor. The illuminating system 17 comprises a dichroic mirror 170 placed on the optical path of the light emitted by the source S. Said light is partially redirected toward the sensor 18 through a filter in order to analyze and determine the corresponding temperature.

One particular optical solution consists in employing fibers comprising a distributed Bragg grating, in order to measure the wavelength of the emitted light signal and to deduce therefrom the temperature of the crystal 13. This solution is well known in the prior art.

As a variant embodiment, the employed temperature sensor is a thermocouple, i.e. a PT100 or PT1000, deposited in thin-film form and incorporated into the heat exchanger.

For an application to the treatment of cancer, one variant embodiment of the device of the invention consists in incorporating at the end of the stem a system that is able to be installed in the exeresis cavity and that conforms as well as possible to the shape of the latter. It is for example a question of a balloon that is inflatable with liquid, such as saline solution. The shape of the heat exchanger will also be adapted to conform as best as possible to the shape of the tumor (shape determined by preoperative imaging). For this application, the cooling device may operate continuously, and not employ detecting means 20 such as described above.

Advantageously, the detecting means 20 described above will possibly be incorporated into the cooling device of the invention. Said means will for example be positioned at the far end of the stem in proximity to the cold finger. The device 1 will then perform both the detection function and the localized cooling treatment function.

Generally, the cooling device 1 thus has the following particularities:
Suppleness to avoid damaging the tissues of the living being;
Presence of a far end of rounded or oblong shape in order to easily penetrate into tissue and to avoid lesions;
Anti-crush property in order to avoid rupture of the waveguide during the surgery;
The cooling element defines a cooling zone the area of which is adapted to the zone to be treated;

Using a crystal of Yb:YLF doped with between 5% and 10% Yb of 5 to 12 mm length it is possible to expect to obtain a cooling efficiency of 1 to 2%. Depending on the power of the excitation laser, it may therefore be possible to obtain cooling powers of a few mW to a few hundred mW.

The invention claimed is:

1. A device for cooling an organ locally, comprising:
   an elongate stem comprising a far end intended to make contact with an organ to be cooled and comprising:
      a cooling element comprising a cold finger,
      a crystal that has a capacity to cool via excitation at a set excitation wavelength, said crystal being positioned adjacent to said cooling element,
      an optical guide that is able to convey a light signal at said excitation wavelength and that opens onto said crystal,
   an illuminating system comprising at least one light source, which light source is arranged to emit said light signal.

2. The device as claimed in claim 1, further comprising a cavity in which said crystal is housed.

3. The device as claimed in claim 2, wherein the cooling element comprises a heat exchanger that is arranged between the cold finger and the cavity housing the crystal.

4. The device as claimed in claim 1, further comprising at least one second optical guide that is arranged along the stem and that opens onto said crystal so as to remove or monitor the fluorescence level emitted by the excitation of the crystal.

5. The device as claimed in claim 1, further comprising a processing and control unit arranged to control said illuminating system.

6. The cooling device as claimed in claim 5, further comprising a temperature sensor arranged to determine the temperature of the crystal.

7. The cooling device as claimed in claim 6, wherein said temperature sensor comprises means for determining the temperature of the crystal from the wavelength of the light signal emitted by the light source.

8. The device as claimed in claim 1, wherein the stem is formed by an overmolding made of silicone or polyurethane.

9. The device as claimed in claim 1, wherein the crystal is of Yb:YLF, Zb:LANP or Tm:Yb:YLF type.

10. The device as claimed in claim 1, wherein the light source is chosen among:
    a laser diode,
    a fiber laser,
    a DPSS laser, or
    an OPS laser.

* * * * *